United States Patent
Xu et al.

(10) Patent No.: US 11,998,016 B2
(45) Date of Patent: Jun. 4, 2024

(54) **USE OF *CHAETOMIUM GLOBOSUM* STRAIN IN CONTROLLING FUSARIUM CROWN ROT OF WHEAT**

(71) Applicant: Institute of Plant Protection, Henan Academy of Agricultural Sciences, Henan (CN)

(72) Inventors: Fei Xu, Henan (CN); Yuli Song, Henan (CN); Junmei Wang, Henan (CN); Jiaojiao Zhang, Henan (CN); Zixing Han, Henan (CN); Yahong Li, Henan (CN); Ruijie Shi, Henan (CN); Lijuan Li, Henan (CN); Lulu Liu, Henan (CN)

(73) Assignee: Institute of Plant Protection, Henan Academy of Agricultural Sciences, Zhengzhou (CN)

( * ) Notice: Subject to any disclaimer, the term of this patent is extended or adjusted under 35 U.S.C. 154(b) by 125 days.

(21) Appl. No.: 17/233,732

(22) Filed: Apr. 19, 2021

(65) Prior Publication Data
US 2022/0053771 A1    Feb. 24, 2022

(30) Foreign Application Priority Data
Aug. 18, 2020   (CN) .......................... 202010832744.5

(51) Int. Cl.
*A01N 63/30*   (2020.01)
*A01N 25/04*   (2006.01)
*C12N 15/00*   (2006.01)

(52) U.S. Cl.
CPC ............. *A01N 63/30* (2020.01); *A01N 25/04* (2013.01); *C12N 15/00* (2013.01)

(58) Field of Classification Search
CPC ........ A01N 25/00; A01N 25/04; A01N 63/30; A01N 65/00; A01N 63/00; A01N 63/20; A01P 3/00
USPC .......................................................... 504/100
See application file for complete search history.

(56) References Cited

U.S. PATENT DOCUMENTS 5,041,290 A * 8/1991 Gindrat .................... A01C 1/06
47/DIG. 9

OTHER PUBLICATIONS

M.R. Fernandez et al., Root and Crown Rot of Wheat ,Prairie Soils & Crops Journal, vol. 4 .• 2011, pp. 151-157.*

* cited by examiner

*Primary Examiner* — Audrea B Coniglio
(74) *Attorney, Agent, or Firm* — Morse, Barnes-Brown & Pendleton, P.C.; Martin Z. Zhang, Esq.

(57) ABSTRACT

The present disclosure provides use of a *Chaetomium globosum* strain in controlling *Fusarium* crown rot (FCR) of wheat. The *C. globosum* strain under the deposit designation of 12XP1-2-3 is deposited at China General Microbiological Culture Collection Center (CGMCC) on Jan. 23, 2019 with an accession number of CGMCC No. 17183. Field experiments conclude that coating of wheat seeds with *Chaetomium globosum* strain 12XP1-2-3 can reduce diseased stem rate, disease rating, and disease index by 19.0%-41.3%, 43.7%, and 4.7%-45.4%, respectively.

3 Claims, 1 Drawing Sheet

USE OF *CHAETOMIUM GLOBOSUM* STRAIN IN CONTROLLING FUSARIUM CROWN ROT OF WHEAT

CROSS REFERENCE TO RELATED APPLICATIONS

This application claims priority to Chinese Patent Application No. 202010832744.5, filed on Aug. 18, 2020. The content of this application is hereby incorporated by reference in its entirety.

TECHNICAL FIELD

The present disclosure relates to use of a *Chaetomium globosum* strain in controlling *Fusarium* crown rot (FCR) of wheat.

BACKGROUND

*Fusarium* crown rot (FCR), an important root and crown rot of wheat, can reduce grain weight per ear and 1,000-grain weight. The disease can infect at the seedling, tillering, jointing and adult stages of wheat. Typical symptoms include the browning of the base of the wheat stem to appear the color of soy sauce, and scattered white ears appeared in the field during the filling stage.

Currently, there are no control agents effective against FCR of wheat. Use of the existing chemical agents not only destroy the soil micro-ecological environment and aggravate environmental pollution, but some seed-dressing agents also delay the seeding stage of wheat and affect the emergence. Therefore, the focus of disease control has gradually shifted to biological and agricultural control measures. In the field of crop plant protection, one of the important means in biological control research is to use rhizosphere soil of healthy crop plants to select soil microorganisms with significant biocontrol effects on pathogens and prepare microbial inoculants, and the means is an important way to develop and utilize beneficial microbial resources. *Chaetomium* species are widely distributed in soil and plants. Such microorganisms can produce a variety of antibiotics such as chaetocin and chaetoglobosin, and are widely studied as biocontrol inoculants for plant pathogens. At present, there is no report about the use of isolated *C. globosum* strain in controlling FCR of wheat.

SUMMARY

The present disclosure provides use of a *C. globosum* strain in controlling FCR of wheat. Field experiments conclude that after coating of wheat seeds with *Chaetomium. globosum* strain 12XP1-2-3, diseased stem rate, disease rating, and disease index are reduced by 19-41.3%, 43.7%, and 4.7-45.4%, respectively.

The present disclosure provides use of a *C. globosum* strain in controlling FCR of wheat;
  herein, the *C. globosum* strain under the deposit designation of 12XP1-2-3 is deposited at China General Microbiological Culture Collection Center (CGMCC) on Jan. 23, 2019 with an accession number of CGMCC No. 17183.

The present disclosure further provides use of a biocontrol agent containing the above *C. globosum* strain in controlling FCR of wheat.

The biocontrol agent may be prepared by: multiplying the *C. globosum* strain to obtain a spore suspension, and dispersing the spore suspension in a sodium carboxymethyl cellulose solution to obtain the biocontrol agent.

Preferably, the sodium carboxymethyl cellulose solution may have a mass fraction of 4%, and the spore suspension and the sodium carboxymethyl cellulose solution may have a volume ratio of 3:1.

In the specific use of the above biocontrol agent, wheat seeds are coated at a coating concentration of $5.0\text{-}5.3\times10^4$ ascospores per seed.

Deposit of Biological Material

Biomaterial: *Chaetomium globosum* 12XP1-2-3; Taxonomic designation: *Chaetomium globosum*, deposited at the China General Microbiological Culture Collection Center (CGMCC), Institute of Microbiology Chinese Academy of Sciences, NO. 3, Yard 1, West Beichen Road, Chaoyang District, Beijing, with accession number of CGMCC No. 17183.

Compared with the prior art, the present disclosure has the following beneficial effects:

The *C. globosum* strain 12XP1-2-3 provided by the present disclosure may be used to control FCR of wheat. Field experiments conclude that after seed dressing with the *C. globosum* strain 12XP1-2-3, the diseased stem rate, disease rating, and disease index of wheat may be reduced by 19-41.3%, 43.7%, and 4.7-45.4%, respectively.

BRIEF DESCRIPTION OF THE DRAWINGS

FIG. 1 shows the plate antagonistic effect of *C. globosum* strain 12XP1-2-3 on *Fusarium pseudograminearum* G14LY24-2.

DETAILED DESCRIPTION

The present disclosure will be further described in detail below in conjunction with specific examples, and these examples are intended to understand, not to limit, the protection scope of the present disclosure.

Example 1

Isolation of *C. globosum* Strain 12XP1-2-3

At the wheat filling stage, uninfected plants were collected from a field with take-all of wheat in Xiping County, Henan Province, and packed in paper bags. The samples were stored in a refrigerator at 4° C. The roots of the samples were rinsed; 2-3 cm wheat root tissue was sampled, surface disinfected with 75 wt % absolute ethanol for 10-30 s and 1% NaClO for 1.5 min, and rinsed with sterile water thrice; after blotting up water with sterile filter paper, the wheat root tissue was cut into small sections of about 0.5 cm, and placed on a potato dextrose agar medium (PDA, raw material composition: peeled potato 300 g, dextrose 20 g, agar 20 g, and distilled water 1,000 ml) plate with sterile tweezers; after culturing at 20° C. for 5-7 days, marginal hyphae were picked to grow on a new PDA plate. After 5-7 days under the same conditions, hyphal pellets with uniform colonies were picked, cultured on PDA slant, and stored at 4° C.

Example 2

DNA Extraction of *C. globosum* Strain 12XP1-2-3

*C. globosum* strain 12XP1-2-3 was picked on a PDA medium, and cultured at 20° C. for 5-7 days; five marginal hyphal pellets were picked and placed evenly on a PDA plate covered with sterilized cellophane. After 3-5 days, hyphae were scraped with a small sterilized iron shovel, quick-frozen with liquid nitrogen, and stored in a refrigerator at −20° C. When extracting DNA, 20-25 mg of hyphae were taken out into a pre-cooled 1.5 ml EP tube; a little liquid nitrogen was added, and the hyphae were ground into a powder using a pre-cooled iron nail in the EP tube; 500 μl of Extraction Buffer (50 mM Tris-HCl (pH 8.0), 150 mM NaCl, and 100 mM EDTA (8.0)) was added, pellets were shaken, suspended and mixed well on a vortex shaker; subsequently, the pellets were mixed with 25 µl of preheated (20 wt %) sodium dodecyl sulfonate, inverted to mix well, and placed in a 37° C. water bath for 1-3 h; subsequently, the mixture was mixed with 75 µl of 5 M NaCl, and inverted to mix well; the mixture was mixed with 65 µl of CTAB/NaCl (10% CTAB and 0.7 M NaCl) solution, and placed in a 65° C. water bath for 30 mM; the mixture was mixed well with an equal volume (700 µl) of Tris-phenol: chloroform: iso-amyl alcohol (25:24:1) mixture and centrifuged at 10,000 rpm and 4° C. for 10 mM, and a supernatant (550 µl) was transferred to another EP; the supernatant was mixed with 0.6 times volume of pre-cooled isopropanol (330 µl), pelleted at −20° C. for 10 mM, and centrifuged at 10,000 rpm and 4° C. for 10 mM, a supernatant was discarded; the pellets were washed twice with 70 wt % ethanol, and air-dried on a clean bench for 5-10 min; the dried pellets were dissolved in an appropriate amount of sterile ddH$_2$O and stored at −20° C.

Example 3

Molecular Identification of *C. globosum* Strain 12XP1-2-3

In this experiment, primers ITS1 (5'-TCC GTA GGT GAA CCT GCG G-3') and ITS4 (5'-TCC TCC GCT TAT TGA TAT GC-3') were used to amplify DNA fragments containing ITS1, 5.8S rDNA and ITS2 in the test strain. For the system, refers to Daval et al. (2010) Amplification conditions were as follows: PCR program was: 95° C. for 3 mM; 35 cycles of 95° C. for 45 s, 50° C. for 30 s, and 72° C. for 1 min; 72° C. for 10 mM. After PCR products were sequenced, BLAST sequence alignment analysis was performed in NCBI. The sequence alignment result concluded that the biocontrol inoculant 12XP1-2-3 was *C. globosum*.

TABLE 1

PCR system

| Component | Concentration | Volume (µL) |
|---|---|---|
| 10× PCR Buffer | 10 mM | 5.0 |
| dNTP Mix | 10 mM | 1.0 |
| TaqDNA polymerase | 5 U | 0.5 |
| Primer 1 | 20 µM | 1.0 |
| Primer 2 | 20 µM | 1.0 |
| DNA Template | 10-50 ng/µl | 1.0 |
| ddH$_2$O | Pure water | 40.5 |
| Total volume (µl) | | 50.0 |

Example 4

Plate Antagonistic Effect of *C. globosum* Strain 12XP1-2-3 on *F. pseudograminearum*

The *C. globosum* strain 12XP1-2-3 was picked with a sterile toothpick and activated on a PDA; the culture condition was 25° C. on 12 h light/12 h dark cycle. The wheat crown rot fungus G14LY24-2 was activated on a PDA; the culture condition was 25° C. without light. When colonies were close to the edge of a Petri dish (7 days later), a puncher with an inner diameter of 0.5c m was used to beat the edges of the colonies of *C. globosum* and wheat crown rot fungus into a plurality of mycelium discs. Two sections were marked 2.5 cm away from the center of the PDA Petri dish; mycelium discs of *C. globosum* and wheat crown rot fungus were placed at the marked points, respectively, with a distance of 5 cm between both centers; only a mycelium disc of wheat crown rot fungus was placed in the blank control, and cultured at 25° C. without light. Three days later, the growth of the wheat crown rot fungus was determined by streaking. The results are shown in FIG. 1. The results showed that the inhibition rate of the *C. globosum* strain 12XP1-2-3 against the *F. pseudograminearum* G14LY24-2 on the plate was 30.3%.

Example 5

Field effect of seed coating with *C. globosum* strain 12XP1-2-3 on controlling FCR of wheat
1. Field Control Effect of *C. globosum* on FCR of Wheat
1.1. Culture of Inoculum of *F. pseudograminearum*
Wheat grains are soaked for 12 h, sterilized for 60 min, allowed to stand for two days, sterilized for 30-60 min, and cooled for later use. *Fusarium pseudograminearum* G14LY24-2 was selected on a PDA plate. After growing for three days, marginal hyphae were picked to grow on a fresh PDA plate. After three days, the hyphal pellets were plated into a wheat grain polyethylene bag with sterilized wheat grains. The hyphal pellets grew at room temperature for two weeks until the fungi grew all over wheat grains, and stored in a refrigerator at 4° C. after air-drying.
1.2. Construction of Field Disease Nurseries
Disease nurseries were constructed in a 1:1 ratio of seed quantity to inoculum volume ratio. The inoculation was located 3-5 cm above the seed. The seeds to be sown and the inoculum were mixed first, and after mixing well, well-mixed sowing materials were sown by a planter.
1.3. Seed Coating with *C. globosum*
Selected *C. globosum* strains were activated on a fresh PDA, and hyphal pellets were picked into 9 cm PDA Petri dishes. After 15 days, perithecia were ground in sterile water using a spreading rod, and ascospore suspension was controlled at about 100 mL, with a concentration of 1.0-2.0×10$^7$ ascospores/mL; in case of a low concentration, the suspension was centrifuged at 3,000 rpm for 5 min, dewatered, and resuspended. 75 mL of fungal suspension (approximately 1.3×10$^7$ ascospores/mL) was mixed with 25 mL of 4 wt % carboxymethyl cellulose salt solution into 100 mL of fungal suspension with 1% carboxymethyl cellulose salt (approximately 1.0×10$^7$ ascospores/mL). 100 mL of 1×10$^7$ ascospores/mL fungal suspension with 1% carboxymethyl cellulose salt was mixed well with 5 kg of wheat seeds. *Chaetomium globosum* strain 12XP1-2-3-coated seeds were rinsed and spread on a plate to count spores on the seed surface, which was 5.0-5.3×10$^4$ ascospores per seed. The wheat cultivar in 2018 was "Bainong 207", the wheat cultivar in 2019 was "Aikang 58", the control agent was 30 g/L difenoconazole, and the seeds were dressed in an agent-to-seed ratio of 1:333.
1.4. Data Investigation and Recording
Field sampling method: At the seedling stage, the emergence rate was investigated, and the plant height, tap root length, fresh weight, dry weight, and colonization ability of *C. globosum* were measured; at the tillering stage, the morbidity was investigated, and the plant height, tap root length, fresh weight, dry weight, tiller number, and colonization ability of *C. globosum* were measured; the morbidity was investigated at the jointing stage; the white ear rate was investigated at the filling stage. The method was to investigate the number of white heads and total number of ears per 1 m2 plot and calculate the white ear rate of the plot. The diseased stem rate was investigated at the maturing stage; 20 stems were sampled at five points in each plot, a total of 100 stems for each treatment were brought back to the laboratory, and leaf sheaths were removed thoroughly to determine the disease rating.
The grading standard for adult stage was as follows: 0=no disease; 1=browning in the first node; 2=browning in the second node; 3=browning in the third node; 4=browning in the peduncle or white ears at the filling stage; and 5=diseased plant without ear bearing. The yield was determined during harvest. The results are shown in Table 2.

TABLE 2

Effects of seed coating with *C. globosum* on controlling FCR of wheat at the wheat filling stage in 2018 and 2019

| Treatment | "Bainong 207" in Kaifeng in 2018 | | | "Aikang 58" in Wenxian in 2019 | | |
|---|---|---|---|---|---|---|
| | Disease index | Diseased stem rate % | Average disease rating | Disease index | Diseased stem rate % | Average disease rating |
| Difenoconazole | 12.9 | 30.0 | 0.6 | 9.4 | 26.0 | 0.5 |
| 12XP1-2-3 | 14.1 | 33.9 | 0.7 | 17.3 | 40.8 | 0.9 |
| Control | 14.8 | 57.8 | 0.7 | 31.7 | 50.4 | 1.6 |

As can be seen from Table 2, according to the investigation at the filling stage, the wheat cultivar in 2018 is "Bainong 207", in the control treatment, the diseased stem rate is 57.8%, and the average disease rating is 0.7; for the seed coating with *C. globosum* strain 12XP1-2-3, the diseased stem rate and the average disease rating are 33.9% and 0.7, respectively; the wheat cultivar in 2019 is "Aikang 58", in the control treatment, the diseased stem rate is 50.4%, and the average disease rating is 1.6; for the seed coating with *C. globosum* strain 12XP1-2-3, the diseased stem rate and the average disease rating are 40.8% and 1.6, respectively.

It is suggested that coating of seeds with the *C. globosum* strain 12XP1-2-3 provided by the present disclosure can not only reduce the white head rate, but also lower the disease rating and disease index.

It should be noted that the steps and methods adopted in the claims of the present disclosure are the same as those in the above-mentioned examples. In order to prevent repetition, the present disclosure describes preferred examples, but once those skilled in the art learn the basic creative concept, then these examples can be changed and modified additionally. Therefore, the appended claims are intended to be interpreted as including the preferred examples and all changes and modifications falling within the scope of the present disclosure.

Obviously, those skilled in the art can make various changes and modifications to the present disclosure without departing from the spirit and scope of the present disclosure. In this way, if these modifications and variations of the present disclosure fall within the scope of the claims of the present disclosure and equivalent technologies thereof, the present disclosure is further intended to include these modifications and variations.

What is claimed is:

1. A method for controlling *Fusarium* crown rot (FCR) of wheat, the method comprising applying a *Chaetomium globosum* strain or a biocontrol agent containing the *Chaetomium globosum* strain to a FCR fungus,
    wherein the *Chaetomium globosum* strain is strain 12XP1-2-3 deposited at China General Microbiological Culture Collection Center (CGMCC) on Jan. 23, 2019 with an accession number of CGMCC No. 17183;
    wherein strain 12XP1-2-3 is identified by PCR using sequences ITS1 (5'-TCC GTA GGT GAA CCT GCG G-3') and ITS4 (5'-TCC TCC GCT TAT TGA TAT GC-3') as primers for amplification of DNA fragments containing ITS1, 5.8S rDNA and ITS2 in strain 12XP1-2-3; and
    wherein wheat seeds are coated at a coating concentration of $5.0$-$5.3 \times 10^4$ ascospores per seed.

2. The method according to claim 1, wherein the biocontrol agent is prepared by multiplying the *Chaetomium globosum* strain to obtain a spore suspension, and dispersing the spore suspension in a sodium carboxymethyl cellulose solution to obtain the biocontrol agent.

3. The method according to claim 2, wherein the sodium carboxymethyl cellulose solution has a mass fraction of 4%, and the spore suspension and the sodium carboxymethyl cellulose solution have a volume ratio of 3:1.

* * * * *